US010443738B2

(12) United States Patent
Durst et al.

(10) Patent No.: US 10,443,738 B2
(45) Date of Patent: Oct. 15, 2019

(54) MAGNETIC FLUID SEAL FOR IMPLANTABLE DEVICES

(71) Applicants: Christopher A. Durst, Houston, TX (US); Jason J. Heuring, Houston, TX (US); Benjamin A. Hertzog, Houston, TX (US); Yoshinori Mitamura, Sapporo (JP)

(72) Inventors: Christopher A. Durst, Houston, TX (US); Jason J. Heuring, Houston, TX (US); Benjamin A. Hertzog, Houston, TX (US); Yoshinori Mitamura, Sapporo (JP)

(73) Assignee: PROCYRION, INC., Houston, TX (US)

( * ) Notice: Subject to any disclaimer, the term of this patent is extended or adjusted under 35 U.S.C. 154(b) by 0 days.

(21) Appl. No.: 15/627,283

(22) Filed: Jun. 19, 2017

(65) Prior Publication Data
US 2017/0363210 A1   Dec. 21, 2017

Related U.S. Application Data

(60) Provisional application No. 62/351,740, filed on Jun. 17, 2016.

(51) Int. Cl.
*F16J 15/43* (2006.01)
*A61L 2/00* (2006.01)
*A61L 2/20* (2006.01)

(52) U.S. Cl.
CPC .............. *F16J 15/43* (2013.01); *A61L 2/0094* (2013.01); *A61L 2/206* (2013.01); *A61L 2202/21* (2013.01)

(58) Field of Classification Search
CPC ...... F16J 15/43; A61L 2/0094; A61L 2202/21
See application file for complete search history.

(56) References Cited

U.S. PATENT DOCUMENTS

| | | | |
|---|---|---|---|
| 3,620,584 A | 11/1971 | Rosensweig | |
| 4,127,384 A | 11/1978 | Fahlvik et al. | |
| 4,407,508 A * | 10/1983 | Raj | F16J 15/43 277/302 |
| 4,643,641 A | 2/1987 | Clausen et al. | |
| 5,007,513 A * | 4/1991 | Carlson | F16D 37/008 192/21.5 |

(Continued)

OTHER PUBLICATIONS

R. Vazquez et al., Plasma Protein Denaturation with Graded Heat Exposure, Perfusion, 28(6) 557-559, 2013.

*Primary Examiner* — Gilbert Y Lee
(74) *Attorney, Agent, or Firm* — Winstead PC

(57) ABSTRACT

Systems and methods for providing a magnetic fluid (MF) seal suitable for a fluid environment may provide a shaft and a magnet that is cylindrical or ring-shaped. A magnetic fluid may be present between the magnet and shaft. Additionally, pole pieces may also be provided, which are also cylindrical or ring-shaped. These pole pieces are positioned on the shaft so the magnet is sandwiched between the pole pieces. The magnet, pole pieces, and shaft, if magnetic, may attract and retain the magnetic fluid in an annular gap or region between the shaft and the magnet and/or the pole pieces. The magnetic fluid in the annular gap serves as a seal or barrier that prevents fluid from passing through when pressure is below a predetermined level.

20 Claims, 17 Drawing Sheets

(56) References Cited

U.S. PATENT DOCUMENTS 5,660,397 A * 8/1997 Holtkamp .............. C09K 3/10
                                                        277/410
5,686,045 A    11/1997 Carter
7,758,806 B2    7/2010 Zhao

* cited by examiner

MAGNETIC FLUID SEAL FOR IMPLANTABLE DEVICES

RELATED APPLICATIONS

This application claims the benefit of U.S. Provisional Patent Application No. 62/351,740 filed on Jun. 17, 2017, which is incorporated herein by reference.

FIELD OF THE INVENTION

The present invention relates to devices, systems, and processes for a magnetic fluid seal, and more particularly, to a magnetic fluid seal that is suitable for a submerged liquid environment.

BACKGROUND OF INVENTION

Magnetic fluid (MF) seals have been used in air to seal vacuum devices or to protect equipment against dust intrusion. The performance of a MF seal, however, decreases in liquids, often because the magnetic fluid is exposed to the flow field and can be carried away by the liquid the seal is designed to operate in. To our knowledge, a MF seal for use in blood or similar liquids that overcomes such leaking issues, which may lead to clotting blood interfering with normal pump operation, has not yet been developed.

A miniature MF seal that is capable of operating when submerged in a liquid such as blood is discussed further herein.

SUMMARY OF INVENTION

In one embodiment, a MF seal may be utilized for a rotary blood pump or implantable to prevent fluid intrusion into the electromechanical components of the pump or device. The MF seal system or cartridge may comprise a magnet adjacent to one or more pole pieces. The magnet and pole pieces may be generally ring-shaped to fit on a shaft of the pump or device. In some embodiments, the internal diameter may be selected to provide a relatively large gap between the magnet and shaft or housing. Further, the internal diameters of the pole pieces may be beveled. The internal diameter of the pole pieces may transition from a value providing a very small gap between the pole pieces and shaft to a larger diameter. The MF seal may also provide magnetic fluid, which is retained at desired positions(s) of the annular gap between the shaft/housing and the pole pieces and magnet. In some embodiments, a shield may be provided, which may provide a magnetic fluid reservoir. Magnetic fluid reservoirs may optionally be built into the pole pieces, magnets, or other components of the system. The system may also optionally comprise removable components that confine the magnetic fluid to certain locations at certain times.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1A:
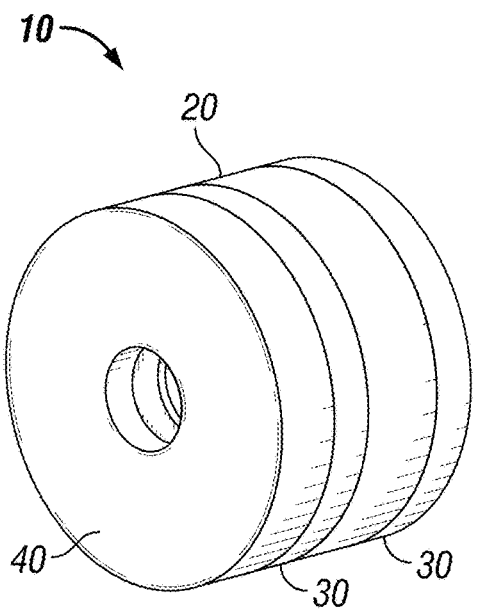
FIGS. 1A-1D: A & B—Magnetic seal "cartridge" or system with tapered pole pieces and shield to minimize test liquid interaction with magnetic fluid. Shield/Trap can act as reservoir for excess magnetic fluid. C & D—Magnetic seal "cartridge" as in A & B, but pole pieces contain integral features to capture magnetic fluid either by surface tension of liquid or as liquid is displaced away from poles during sterilization.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise. Additionally, in light of the various embodiments discussed herein "/" may be utilized to denote alternative arrangements corresponding to the different embodiments.

Systems and methods discussed herein may utilize a magnetic fluid (MF) seal in a liquid environment. In particular, these systems and method are of great interest for devices to be implanted in the human body. It is known that some implanted devices can result in undesirable damage to biological cells. As a nonlimiting example, exposing blood to moving parts or high temperature parts of a heart pump can activate biochemical pathways that result in dangerous and undesirable clotting.

In some embodiments, a MF fluid seal may utilize a magnet positioned on a shaft of a rotating device, such as a pump or the like. The magnet is cylindrical or ring-shaped, and may be further sized to have an internal diameter sized to provide a desired gap between shaft and internal diameter of the magnet, or alternatively, a desired gap between the housing and outer diameter of the magnet. The MF fluid seal also provides one pole pieces, wherein the magnet is adjacent to or sandwiched in between the pole pieces. Pole pieces may be generally cylindrical or ring-shaped. In some embodiments, the diameter of the pole pieces, internal or outer depending on the embodiment, may be vary (e.g. by beveling) near the annular gap to concentrate the magnetic field. The sloping face of the pole pieces may be positioned to face the magnet when sandwiching the magnet. Further, the bevel of the pole pieces may start at an internal/outer diameter approximately equal to the magnet's internal/outer diameter and increase/decrease towards the shaft or housing. The MF fluid seal may also provide a magnetic fluid present in at least a portion of an annular gap between the magnet & pole pieces and the shaft/housing. It shall be apparent to one of ordinary skill in the art from further discussion herein that the magnet and pole pieces create a magnetic field of greatest intensity where gaps between the pole pieces and the shaft is smallest, thereby retaining the magnetic fluid in such gaps. The retention of the magnetic fluid in such gaps prevents other fluids, such as blood, from passing through the annular gap. The MF fluid seal and shaft may be incorporated in a housing where one end of the system is isolated from the other fluids present at an opposite end. In some embodiments, a shield may also be placed on the shaft. The shield is non-magnetic may serve as a reservoir for magnetic fluid. The shield may be general cylindrical or ring-shaped, but the internal portion of the shield may be shaped to provide a magnetic fluid reservoir region. The magnetic reservoir region may be any suitable shape. As a nonlimiting example, a predetermined width or thickness of an internal portion of the shield may have a larger diameter than an exterior portion, and thus, the reservoir region may be ring-shaped. In some embodiments, the external surface (s) further away from the magnet of one or more of the pole pieces may be patterned to provide a magnetic fluid reservoir region. The reservoir region may be any suitable shape. As a nonlimiting example, the reservoir region may be a star-shaped. Such reservoir regions may optionally be built into the pole pieces themselves.

In one embodiment, a MF seal may be utilized for a rotary blood pump to prevent fluid intrusion into the electromechanical components of the pump. The MF seal may provide lower friction compared to conventional seals, such as lip seals. In turn, lower frictional losses will yield lower torque requirements for the drive system. Due to the low friction of a magnetic fluid seal, less heat during operation is generated, which is of particular concern to blood-immersed devices, since protein denaturation and clotting can be precipitated by components with temperatures above 43° C. Furthermore, this type of seal will not shed particulates (as a typical mechanical seal would) and could capture any particulates generated by other elements of the electromechanical drive system (such as particles generated by bearing wear). Finally, this design solves an additional heretofore unsolved problem with using MF seals in medical devices by permitting sterilization of the pump system via conventional methods, such as ethylene oxide gas.

A miniature (e.g. φ4×3.5 mm) MF seal is provided that operates in a submerged liquid environment and has all of the advantages and attributes described above.

The following discussion may reference specific examples that are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

Figure 1B:
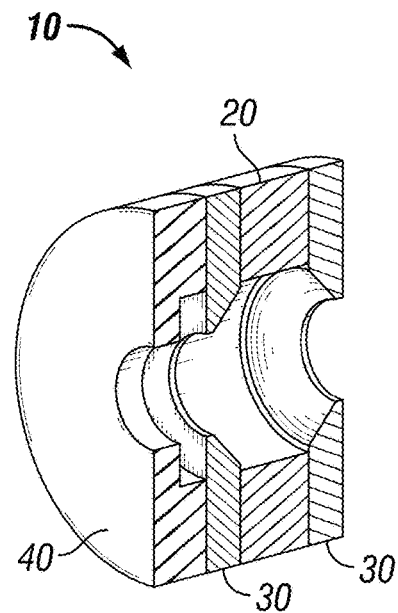
Figure 1C:
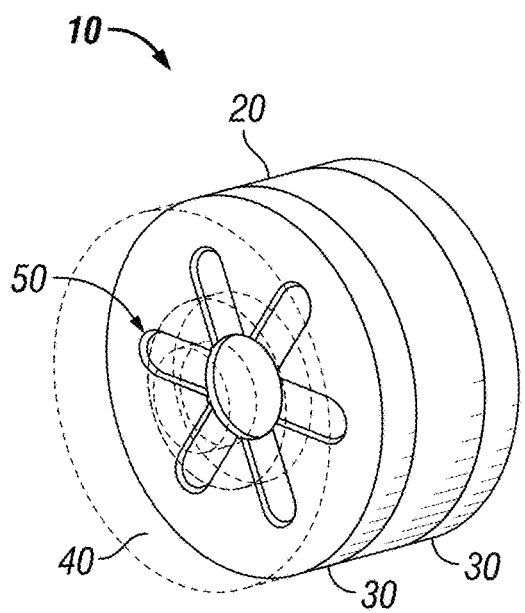
Figure 1D:
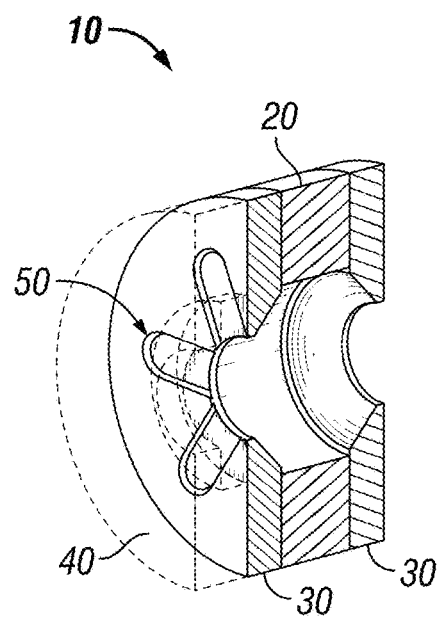

FIGS. 1A-1D show illustrative embodiments of a MF seal system 10. FIG. 1A shows a seal cartridge comprised of two ring-shaped magnetic pole pieces 30, a ring-shaped magnet 20, and non-magnetic shield 40. The pole pieces, magnet, and non-magnetic shield share the same outside diameter and internal diameter; however, the internal diameter of some components may vary in some embodiments as discussed previously and further herein. While the embodiment shown illustrates the magnet 20 and pole pieces 30 as separate components, which may aid ease of fabrication, the magnet and pole pieces may be combined into a single component in other embodiments. FIG. 1B shows a cross section of a similar seal cartridge or system with a beveled pole piece design. FIG. 1C shows a seal cartridge or system where the pole pieces have integral features 50, such as a six pointed star shaped, to retain excess magnetic fluid (the features are on both pole pieces, but are only visible on the closest pole piece). FIG. 1D shows a cross section of the seal cartridge with beveled pole pieces incorporating integral features to from a magnetic fluid reservoir region to contain excess magnetic fluid. In FIGS. 1C and 1D the shield has been made transparent to make the retention features visible.

Figure 1E:
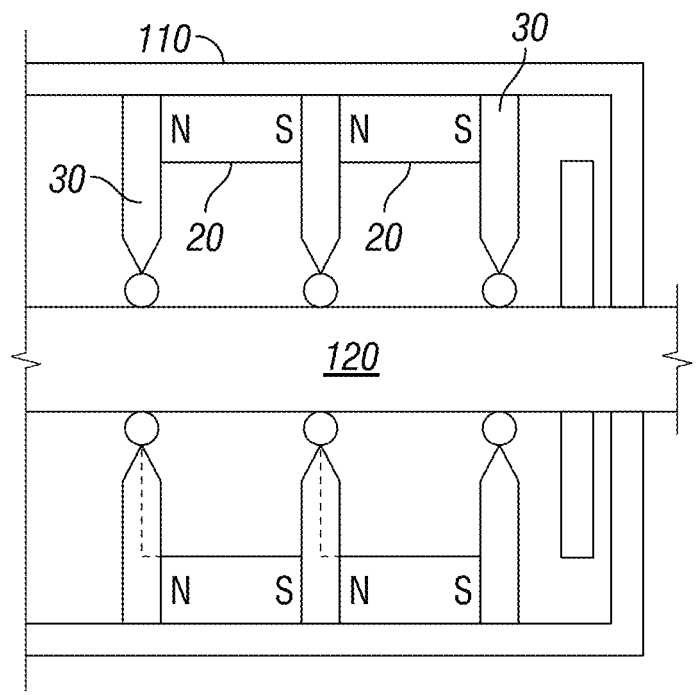
FIGS. 1E-1K show further embodiments of additional magnetic seal arrangements.
Figure 1F:
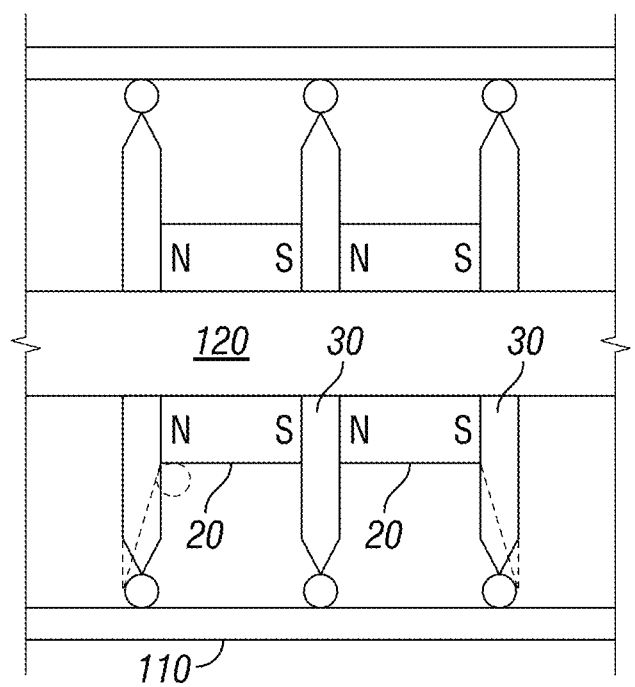

FIGS. 1E-1F show further embodiments of additional magnetic seal arrangements. In some embodiments, the number of magnets and pole pieces may be varied. As nonlimiting examples, two or more magnets may be provided, and three or more pole pieces may be provided. In some embodiments, the magnet(s) and/or pole piece(s) may be affixed to the shaft, or alternatively, the housing. In some embodiments, any suitable beveling arrangement may be provided. While the beveling faces towards the magnet in FIGS. 1A-1D, other nonlimiting examples may include double beveling of both sides of the pole pieces (FIG. 1E) or combinations of single sided beveling and double beveling of the pole pieces. These variations are applicable to any of the embodiments discussed previously or further below.

Figure 1G:
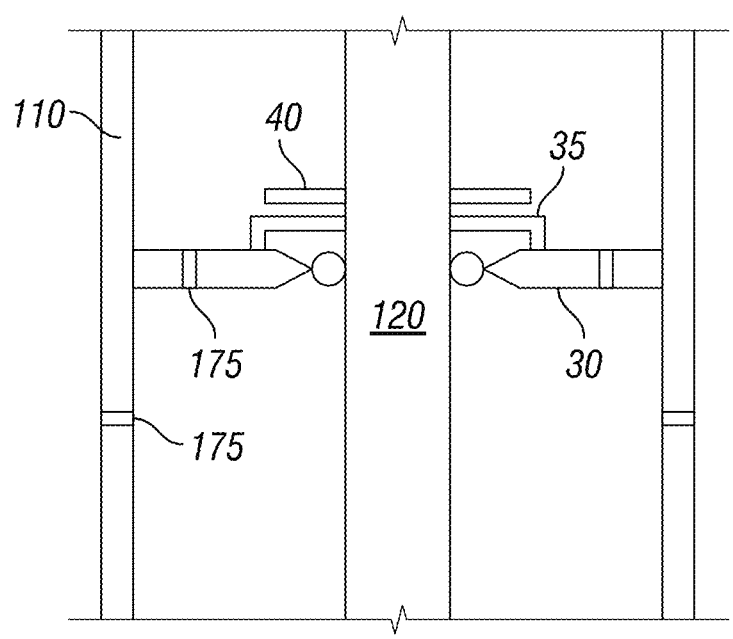

FIG. 1G shows an embodiment with a magnetized shaft and a magnet shaped into a pole piece (which could also be described as a magnetized pole piece), no separate magnet is required. This embodiment also shows two shield pieces, one attached to the shaft 40 and one built into the magnetized pole piece 35. This embodiment also shows gas paths 175 through the magnetized pole piece and through the housing to allow the otherwise isolated region to be sterilized. In use, these gas paths would be closed off after sterilization and immersion in blood by clotting or other biological action. The features of this embodiment may be incorporated in other various embodiments discussed throughout.

Figure 1H:
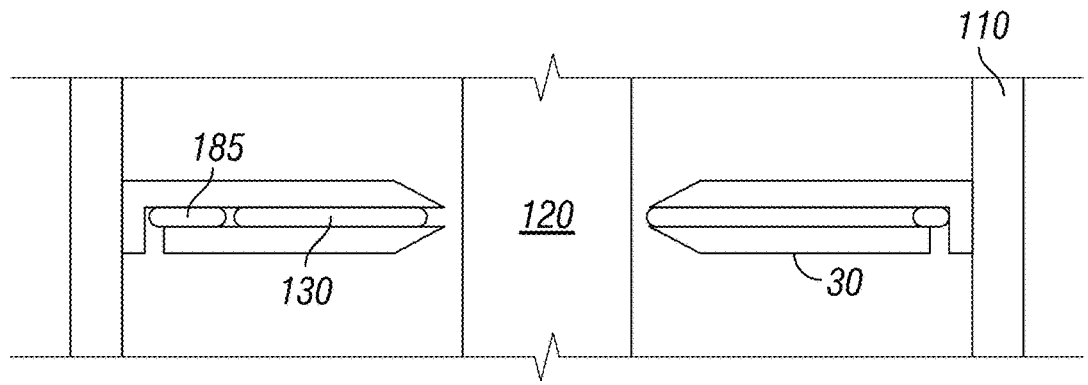
Figure 1I:
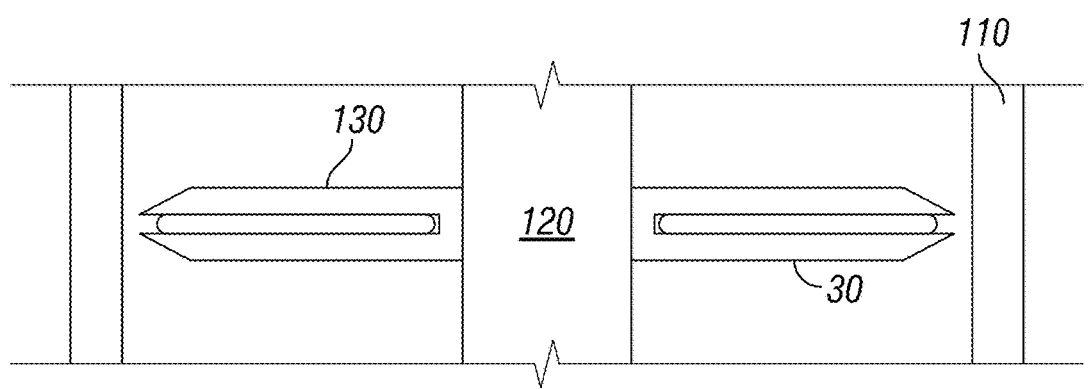

FIGS. 1H-1I show illustrative embodiments which include pole pieces with internal magnetic fluid reservoirs. In these embodiments a separate magnet (not shown) would be included as elsewhere described, or the pole pieces would be magnetized as in FIG. 1G. In FIG. 1H, the pole pieces also include a hydrogel that expands on contact with liquid and thereby pushes the magnetic fluid into the magnetic fluid region. In FIG. 1I, inertial forces move the magnetic fluid into the magnetic fluid region when the motor starts to spin. This movement creates a partial vacuum behind (toward the shaft) the magnetic fluid that prevents the magnetic fluid from moving too far and pulls the magnetic fluid back into the pole piece if the motor stops spinning. The magnetic field may be manipulated through design of the magnet and pole piece to aid in the retention and retraction of the magnetic fluid. The features of this embodiment may be incorporated in other various embodiments discussed throughout.

Figure 1J:
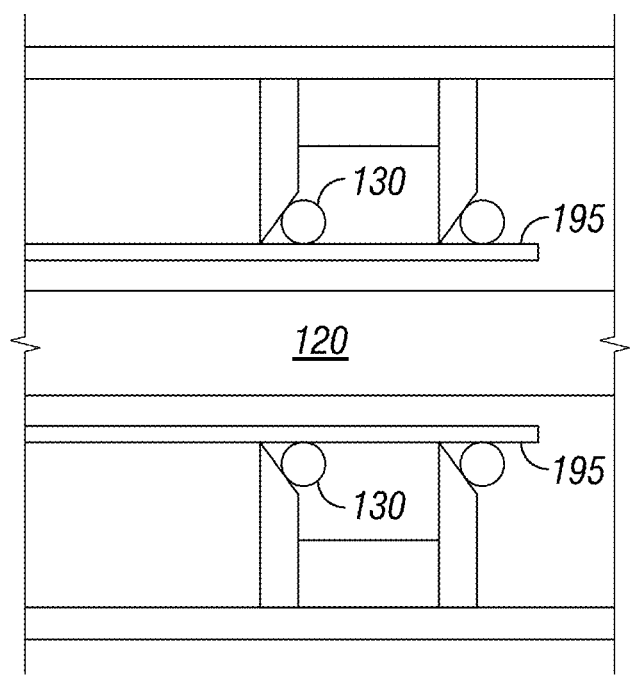
Figure 1K:
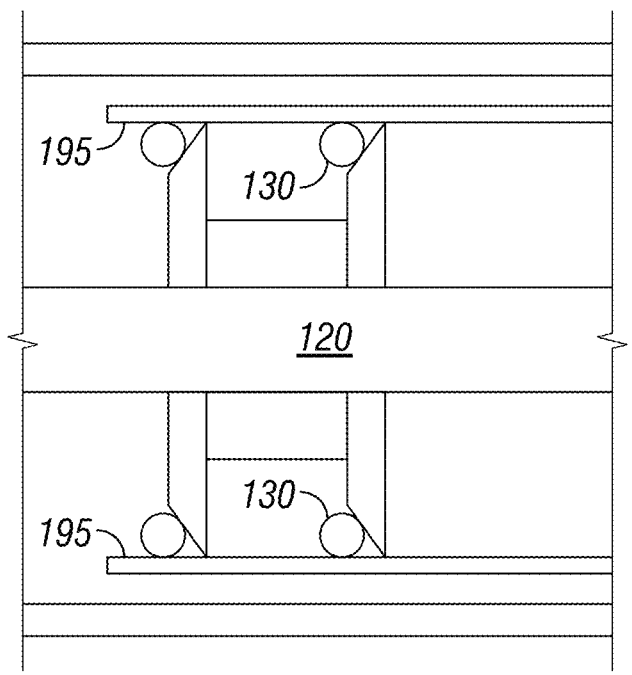

FIGS. 1J-1K show illustrative embodiments that use a temporary sleeve to confine the magnetic fluid away from the magnetic fluid region to allow a gas path for sterilization. After sterilization, the sleeve can be removed to allow the magnetic fluid to move into the magnetic fluid region. The features of this embodiment may be incorporated in other various embodiments discussed throughout.

Figure 2A:
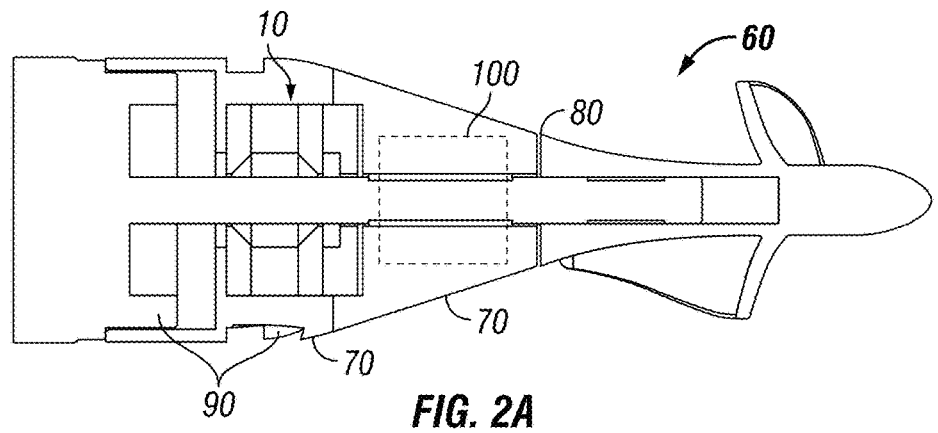
FIGS. 2A-2C: Cross sections of multiple possible embodiments. A, B, & C depict "hybrid" style seals where the magnetic fluid seal is downstream of another sealing element. In these embodiments, the magnetic fluid seal will act to prevent fluid intrusion to the pump when the shaft is stationary, and the additional seal, either on its own or in combination with the magnetic fluid seal, acts to prevent fluid intrusion during operation.
Figure 2B:
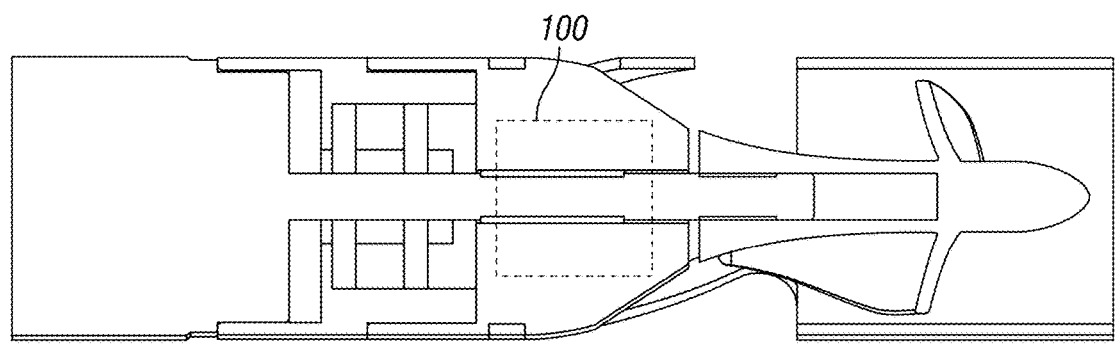
Figure 2C:
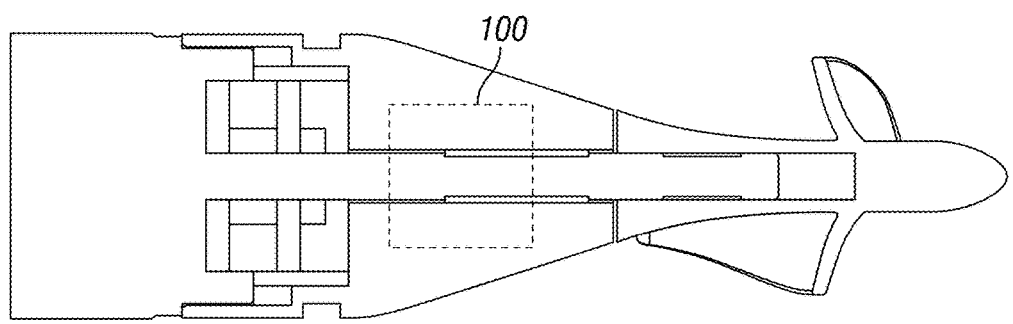

FIGS. 2A-2C show an illustrative embodiment of a MF seal system 10 arranged in a pump 60. FIG. 2A shows a cross section of a pump 60 with a magnetic fluid seal "cartridge" or system 10 (as shown in FIG. 1B) contained within a two-part stator 70. The magnetic fluid seal 10 here prevents fluid intrusion from the impeller-stator gap 80 into the electromechanical components or left side 90 of the pump. This embodiment also shows an optional "hybrid" seal, where an additional seal or group of seals 100 on the shaft could be placed outside the magnetic fluid seal or in a position to interface with the external fluid prior to the MF seal. FIG. 2B shows an alternative embodiment of the magnetic fluid seal cartridge or system, where the pole pieces are standard ring shapes. The "cartridge" or "system" in this embodiment is also contained within a two-part stator. FIG. 2C shows a magnetic fluid "cartridge" or "system" which is integrated into to the motor body. It shall be apparent to one of ordinary skill in the art that MF seal may be utilized with a variety of pumps to isolate a portion or side of the pump from external fluids.

Figure 3:
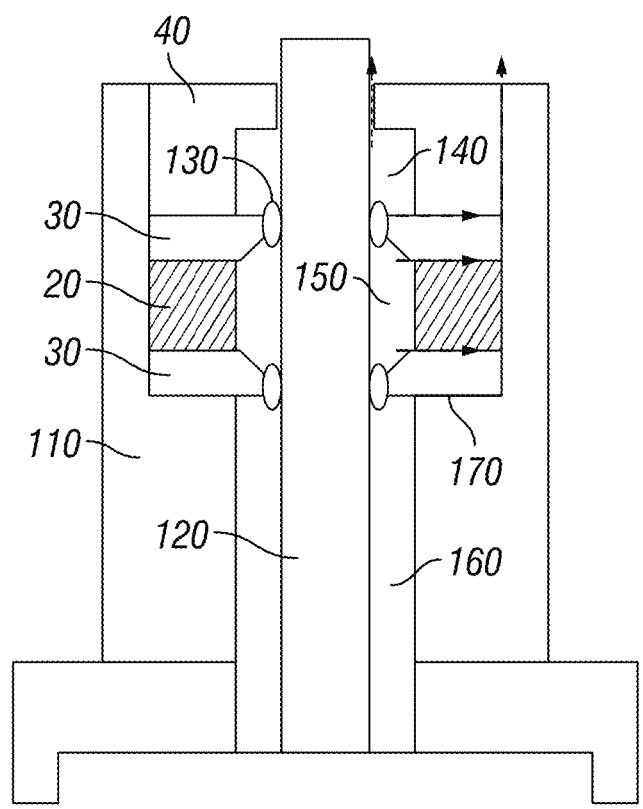
FIG. 3: Cross section of one possible embodiment of a magnetic fluid seal. Blue ellipses indicate magnetic fluids and green arrows indicate possible gas path during sterilization.

FIG. 3 shows a cross-section view of a MF seal system. Systems and methods for providing the MF seal may provide a housing 110 for retaining MF seal, shaft 120, and other components of the pump or device (e.g. motor). The gaps or clearances between the housing and MF seal may be a desired size that allows gas to pass through, but prevents fluid passing through. The housing 110 may also provide features that retain the MF seal in a desired position on the shaft 120 (e.g. FIGS. 2A-2C). The system may provide a magnet 20 that is cylindrical or ring-shaped. In some embodiments, the shaft 120 or a portion of the shaft may also be magnetic. A magnetic fluid 130 may be present in between the magnet 20 and shaft 120. Additionally, pole pieces 30 may also be provided that are also cylindrical or ring-shaped. These pole pieces 30 are positioned on the shaft 120 so the magnet 20 is sandwiched between the pole pieces. The magnet 20, pole pieces 30, and/or shaft 120 may attract and retain the magnetic fluid 130 in annular gap(s) or region(s) between the shaft and the magnet and/or the pole pieces. The magnetic fluid 130 in the annular gap(s) serves as a seal or barrier that prevents fluid from passing through when pressure is below a predetermined level. While the nonlimiting example illustrates the magnetic fluid 130 is present at tips of pole pieces 30 closest to the shaft, it shall be apparent that other areas including the MF reservoir region 140, MF region 150, protected device region 160, or combinations thereof may also provide magnetic fluid 130. Further, in other embodiments, such as shown in FIG. 1F, the magnetic fluid 130 may be between the tip of pole pieces and the housing.

The MF reservoir region 140 may be a large annular region between shaft 120 (or housing 110 when the shield is fixed to the shaft) and the portion of the shield 40 and/or a portion of pole piece 30. The MF reservoir region may also be provided by surface features on either face of or the interior of one or more pole pieces. The MF region 150 is the annular gap or space between the magnet(s) and/or pole pieces present in the system and either the shaft or the housing, depending on the embodiment. The MF region 150 creates the seal that prevent other fluids from entering the device. The protected device region 160 is an internal annular region between the housing 110 and shaft after the magnetic seal that leads to the components of the pump or device that are to be protected from outside fluids, such as blood. In some embodiments, the pole piece closest to the end of the pump to be isolated may be secured in an air tight manner to the housing, such as with an adhesive or the like 170. As such, the annular gap between the pole piece and shaft, which is occupied by magnetic fluid 130, is the only pathway to the protected end of the pump. The remaining magnet 20, other pole piece 30, and shield 40 are retained on the shaft 120 but are optionally not secured together, which allows air pathways (shown by arrows) to form between the components when sterilization is desired. As some embodiments may fix the magnet, pole pieces, and/or shield to the shaft, various combinations of the air pathways may be possible. Holes or other channels may also optionally be used as gas pathways, as described elsewhere herein. In some embodiments, the housing or another component attached to the housing 110 may retain the MF seal components on the shaft 120. In some embodiments, the interior diameter of the pole pieces may be beveled. The beveled portions of the pole pieces may be arranged to face the magnet. In some embodiments, the MF seal may optionally provide a shield or trap that provides a reservoir for excess magnetic fluid when placed adjacent to one of the pole pieces. The shield or trap may be cylindrical or ring-shaped, but a portion of the ring has an increased internal diameter to provide a void of a desired volume that will serve as the reservoir. When the shield or trap is placed against a pole piece, the reservoir region is formed. This reservoir is surrounded by the shaft, shield or trap, and pole piece.

Figure 4A:
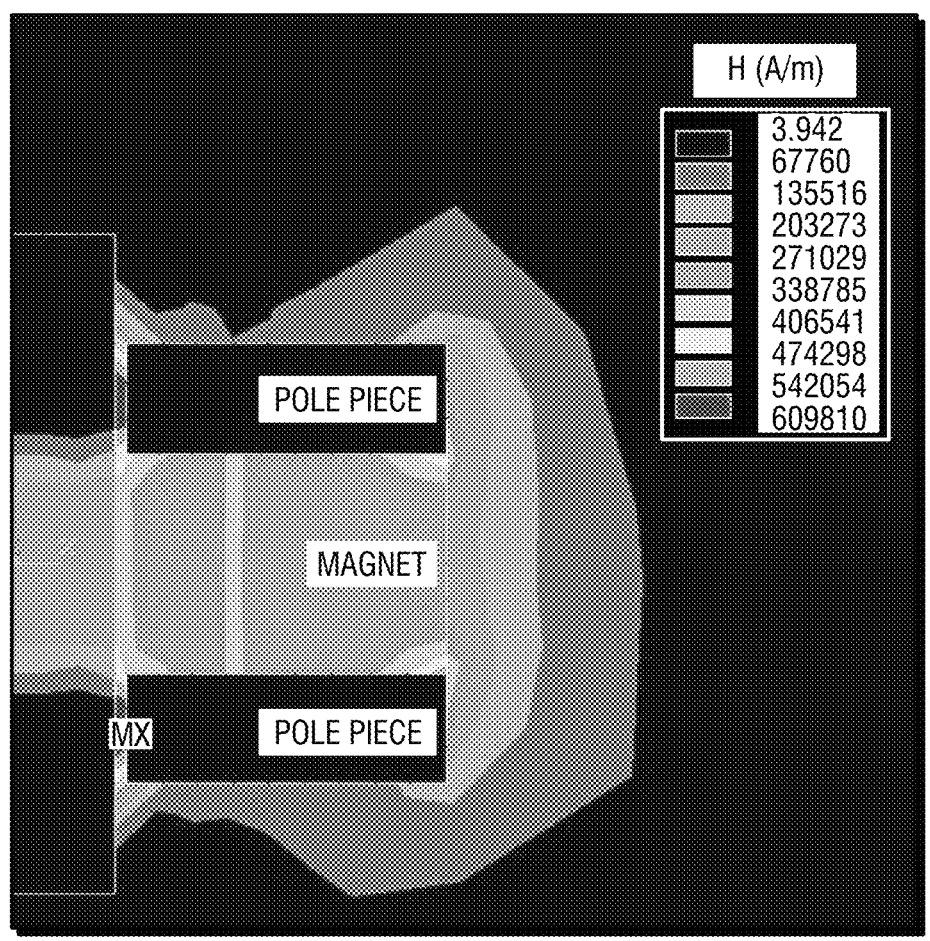
FIGS. 4A-4B: Finite element model of magnetic field (H, A/m) of two possible designs of pole pieces.
Figure 4B:
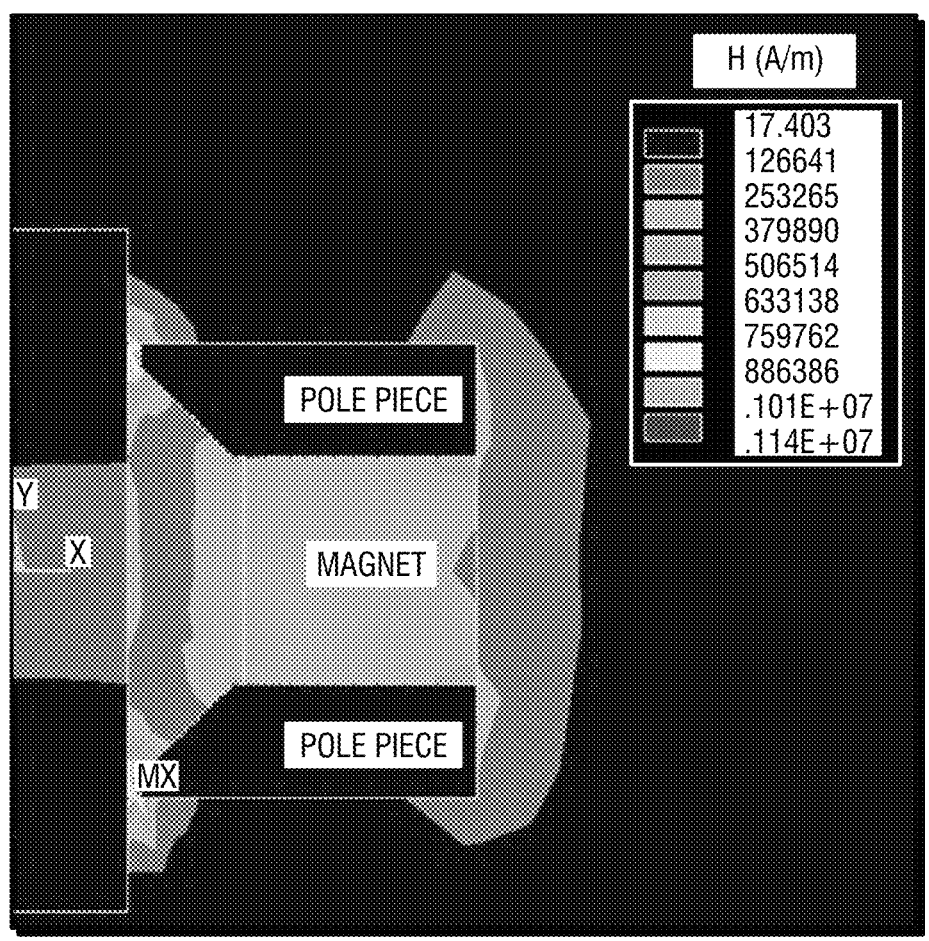

FIGS. 4A-B show finite element models of the magnetic field generated by two different pole piece designs.

Figure 5A:
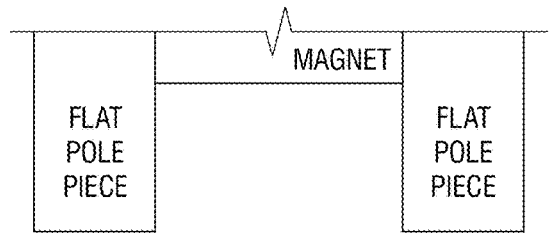
FIGS. 5A-5C: Magnetic field (H, A/m) comparing flat pole piece to beveled or tapered pole piece design.
Figure 5B:
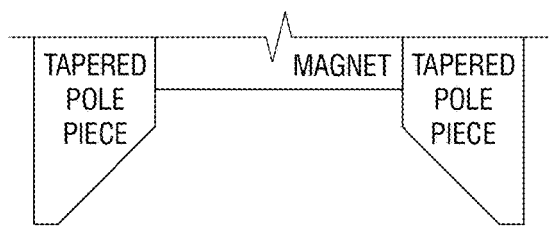
Figure 5C:
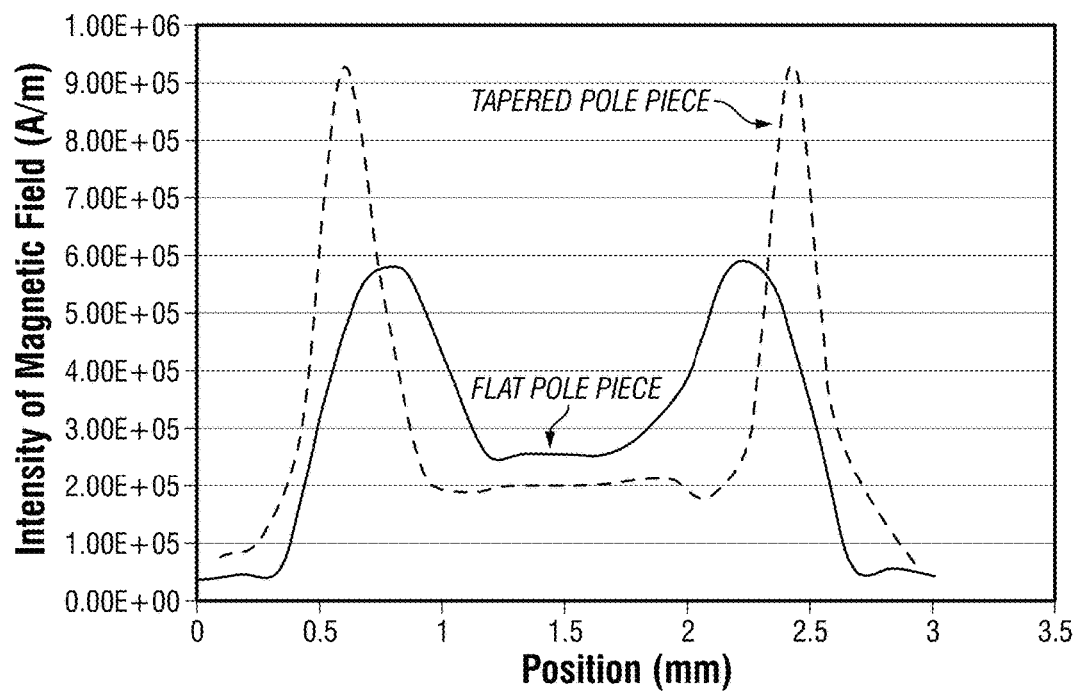

FIGS. 5A-C show two possible pole piece designs and the results of the finite element models. FIG. 5A shows a ring-shaped pole piece design. FIG. 5B shows a tapered or beveled pole piece design. FIG. 5C shows the intensity of the magnetic field generated by each of these designs. The beveled or tapered pole piece design allows for greater intensity at the tips where the pole pieces have the smallest internal diameter.

Figure 6:
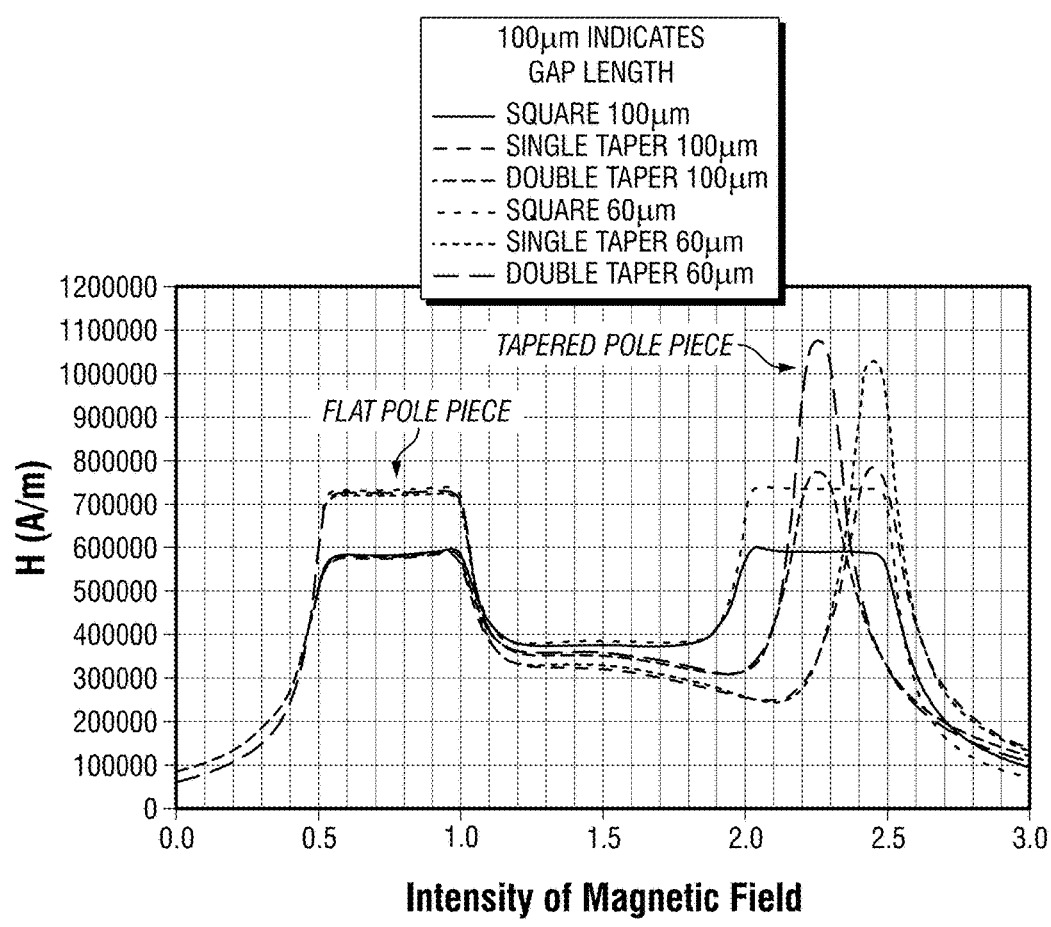
FIG. 6: Magnetic field (H, A/m) comparing three pole piece designs and two pole piece to shaft gap sizes. This simulation demonstrated no substantial benefit from a particular double bevel or tapered design when compared with a certain single bevel design.

FIG. 6 shows the effect of both pole piece geometry and annular gap length between the pole piece and the shaft on the intensity of the magnetic field generated. This simulation demonstrated no substantial benefit from a particular double bevel or tapered design when compared with a certain single bevel design.

Figure 7:
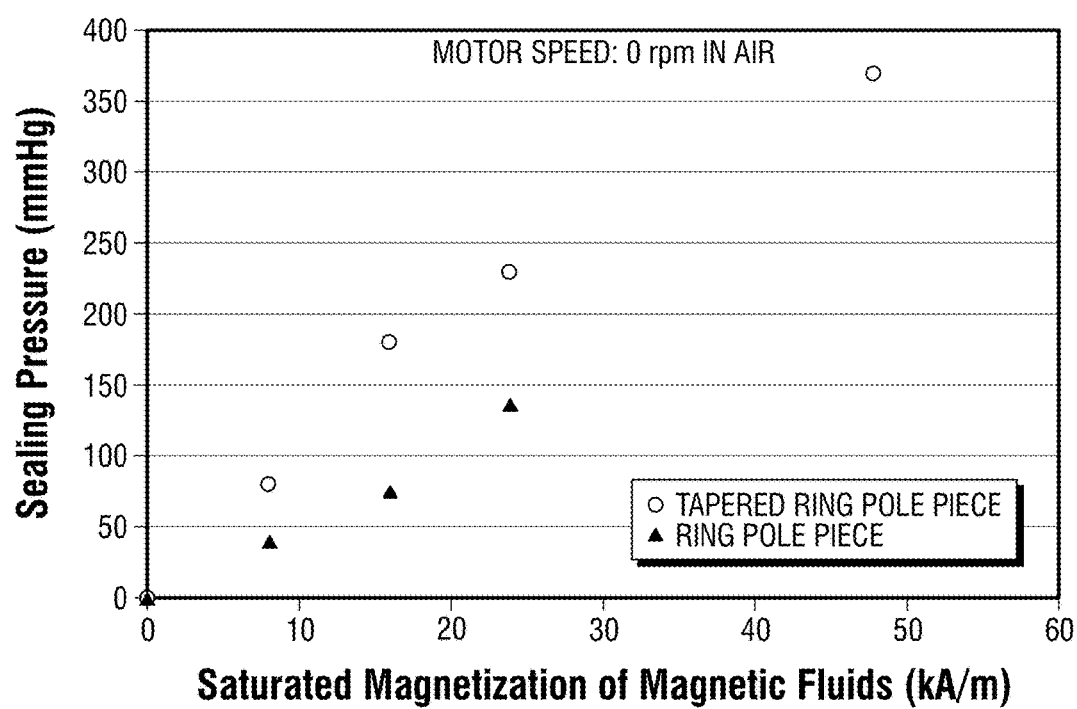
FIG. 7: Relationship between sealing pressure and saturated magnetization for several formulations of magnetic fluids. As saturated magnetization increases, sealing pressure increases. A tapered pole piece yields higher sealing pressure for each fluid formulation than the flat pole piece.

FIG. 7 shows the relationship between sealing pressure and saturated magnetization for several formulations of magnetic fluids. As saturated magnetization increases, sealing pressure increases. A tapered pole piece yields higher sealing pressure for each fluid formulation than the flat pole piece.

Figure 8A:
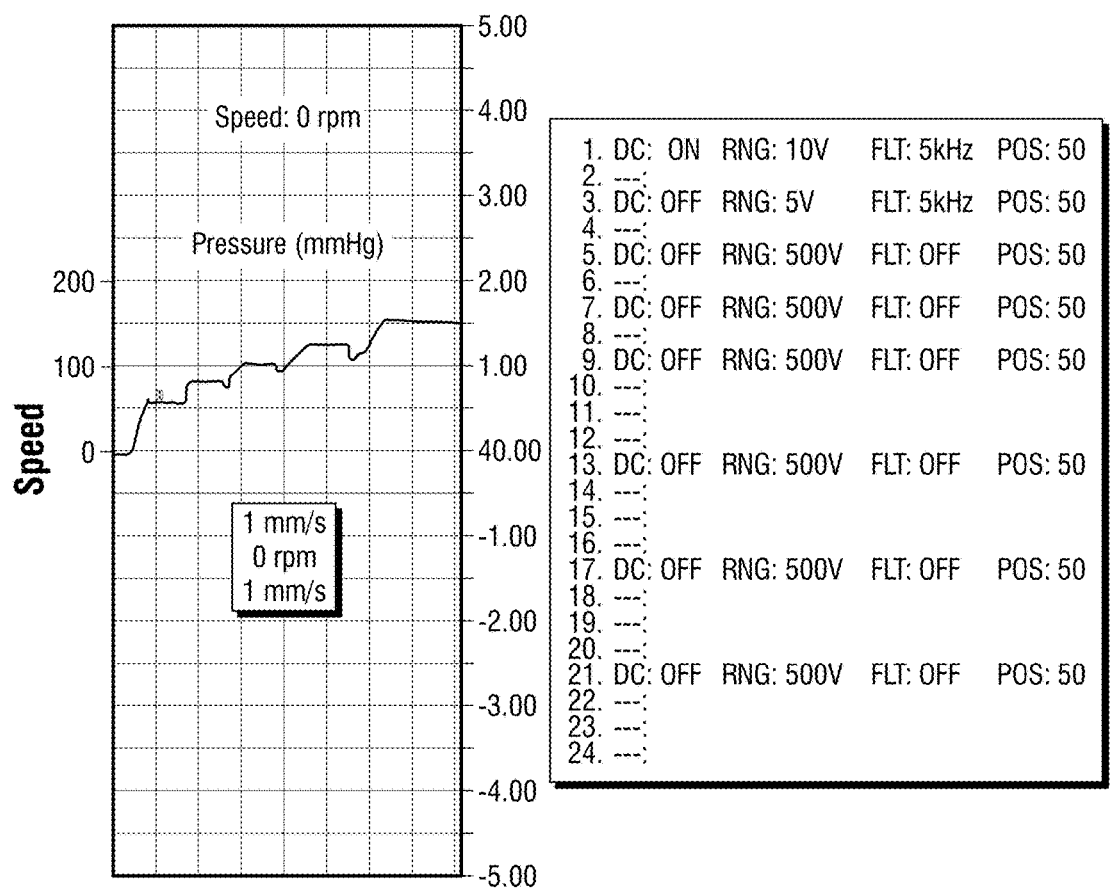
FIG. 8A-8C: A—Pressure measurements before sterilization. The shaft was not rotating, and the seal remained intact at pressures exceeding 150 mmHg. B & C—the pump was subjected to EtO gas sterilization and then the motor shaft was rotated at medium (B) and high (C) speeds (~25 and ~40 krpm respectively) and the seal remained intact against applied pressures exceeding 150 mmHg.
Figure 8B:
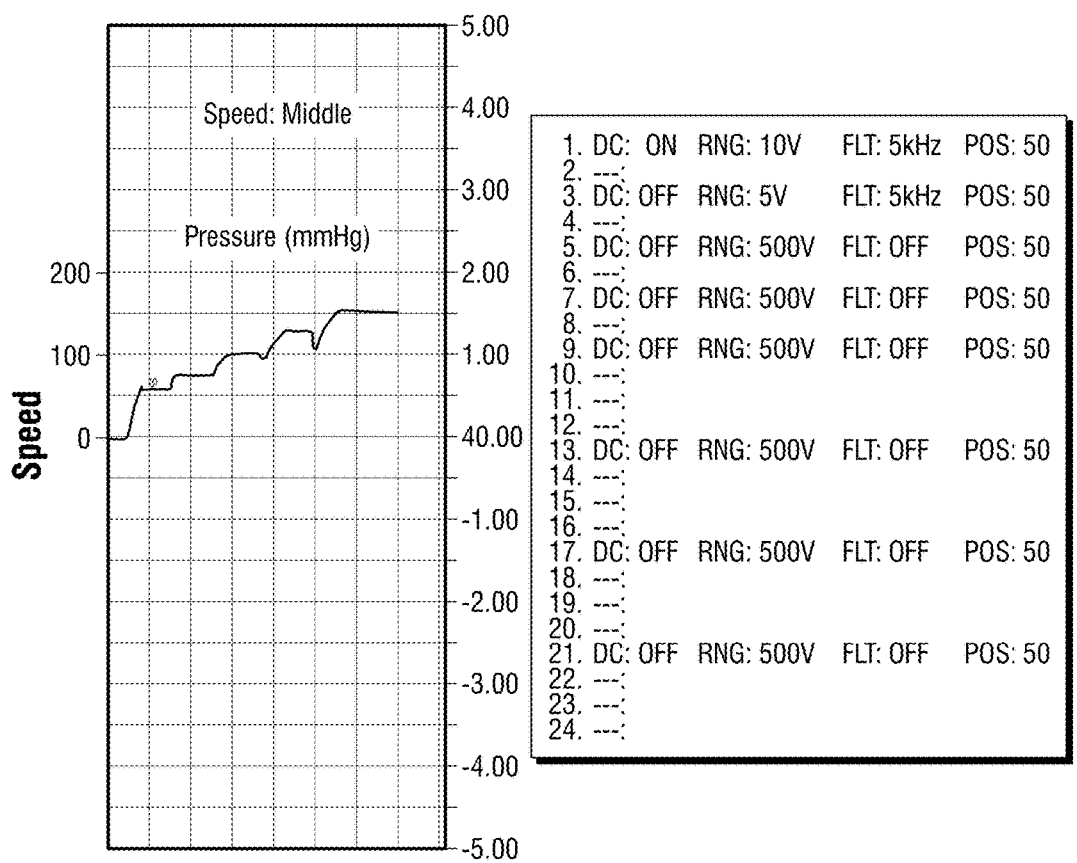
Figure 8C:
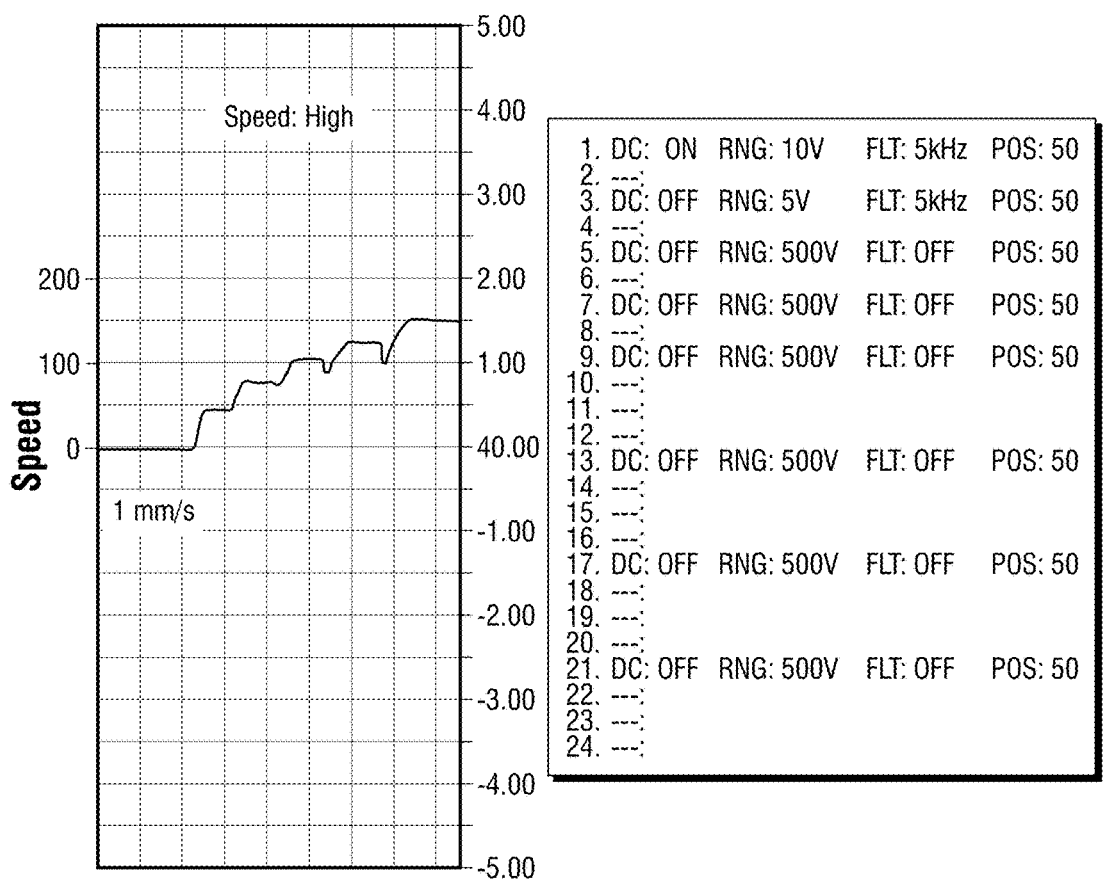

FIGS. 8 A-C shows the sealing pressure obtained from a magnetic fluid seal design. FIG. 8A shows pressure measurements before sterilization. The shaft was not rotating, and the seal remained intact at pressures exceeding 150 mmHg. FIGS. 8B and 8C were obtained after the pump and magnetic fluid seal was subjected to EtO gas sterilization. The pressure measurements were obtained with the motor shaft rotating at medium and high speeds (~25 and ~40 krpm respectively) and the seal remained intact against applied pressures exceeding 150 mmHg.

Figure 9:
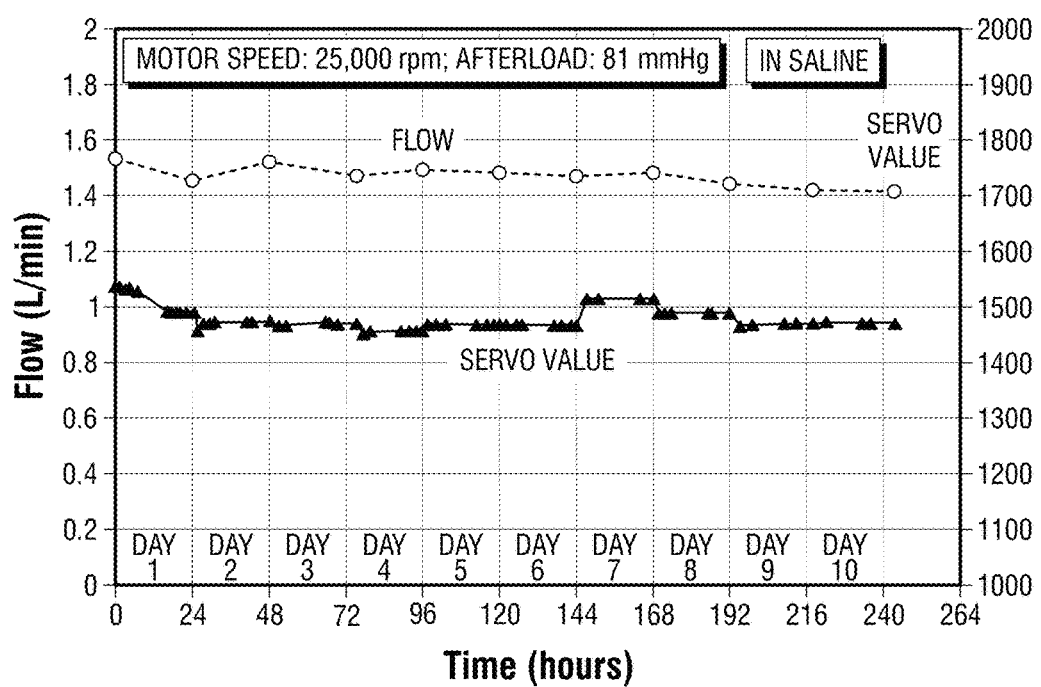
FIG. 9: Magnetic fluid test in saline for 10 days. The magnetic fluid seal was assembled into a pump system that was operated in saline for 10 days with a mean applied pressure of 81 mmHg. Fluid flow was near constant at ~1.5 L/min for the duration of the experiment. No leakage through the seal was observed at the end of 10 days and the experiment was voluntarily terminated.

FIG. 9 shows the results of a magnetic fluid seal test with an operational pump in saline for 10 days. The magnetic fluid seal was assembled into a pump system that was operated in saline for 10 days with a mean applied pressure of 81 mmHg. Fluid flow was near constant at ~1.5 L/min for the duration of the experiment. No leakage through the seal was observed at the end of 10 days and the experiment was voluntarily terminated.

Description of Design/Ideas
Magnetic Fluid

As discussed previously above, the magnetic fluid is attracted to the magnetic components of the MF seal so that it can be retained in a desired region. As discussed previously, the MF region may be present in the annular gap between the magnet & pole piece(s) and the shaft or housing. In some embodiments, the magnetic fluid may be any suitable fluid or lubricant with dispersed ferromagnetic nano-sized or micro-sized particles, either with or without the use of a surfactant. In some embodiments, the fluid or lubricant may be a solvent for the ferromagnetic particles. The magnetic fluid could be optimized for exposure to sterilizing agent (e.g. sterilizing gas, sterilizing liquid, ethylene oxide gas (EtO) or any other suitable sterilizing agent). For example, the fluid could be optimized to reduce or avoid chemical reaction(s) with the sterilizing agent. The magnetic fluid could also be formulated with biocompatible materials, solvents, or surfactants. The size of the magnetic particles could be optimized to prevent agglomeration in blood. The base fluid could be optimized to minimize its interaction with blood, such as by changing its miscibility. The surface tension of the fluid could be optimized to be retained in the reservoir or retention features on the pole pieces.

Magnet

As discussed previously above, the magnet may be cylindrical or ring-shaped in some embodiments. In some embodiments, the shaft may also or alternatively magnetized. As illustrated in FIG. 3, the magnet is positioned coaxially with the shaft and the gap between the shaft and magnet defines a magnetic fluid region where the magnetic fluid is present to create the MF seal. Since the magnet is present to attract the magnetic fluid, it should be formed from permanently magnetized ferromagnetic material(s). The MF seal design may comprise more than one magnet. While the embodiment shown in FIG. 3 show the magnet unattached to the shaft or housing, in some embodiments, one or more magnets may be fixed to the housing (e.g. FIG. 1E) or, alternatively, fixed to the shaft (e.g. FIG. 1F). In embodiments with several magnets, some may be fixed to the housing while others are fixed to the shaft. Magnets may also be shaped to include the pole piece shapes described below, so that no separate pole piece is necessary (as in FIG. 1G).

Pole Piece Design

The pole pieces are formed from ferromagnetic materials and may or may not be permanently magnetized. Several pole piece designs are possible. The simplest design is a ring-shaped pole piece, which may be relatively thin, with a flat cross section. Tapering or beveling the inner circumference to a reduced thickness serves to concentrate the magnetic field, and correspondingly increase the sealing pressure obtained (FIGS. 4A and 4B, FIG. 5). When placed adjacent to the magnet, the sloped portion of the pole pieces may face the magnet. The magnetic field created by the magnet and pole pieces interacts with the magnetic fluid to hold the fluid in the magnetic fluid region. In embodiments where the pole pieces are fixed to a shaft, the outer diameter is beveled, whereas other embodiments may have an internal diameter beveled. The magnetic fluid may stay in the magnetic fluid region until pressure sufficient to force the magnetic fluid out is present, which is controlled by the strength of the magnetic field created by the magnet and directed by the pole pieces (which is in turn driven by the design/geometry of the pole pieces and shaft), the saturated magnetization of the magnetic fluid, and the strength of the magnet.

The magnetic field, and thus the obtained sealing pressure, can be further tuned by varying the annular gap between the inner circumference of the pole pieces and the shaft. In some embodiments, the gap tuning may be optimized to permit gas sterilization (e.g. EtO) of the device. As a nonlimiting example, the MF seal has a predetermined "sterilization pressure" or pressure at which the seal will no longer prevent intrusion and allow the magnetic fluid to migrate from the MF region. The tuning of the sterilization pressure can be set so that it is above pressures encountered during operation, but below pressures utilized when injecting the sterilizing agent into the MF seal (e.g. EtO gas injection into the chamber to be sterilized). This allows gas utilized for sterilization to overcome the sealing pressure, but maintains the seal at lower pressures that the device may operate at.

Reducing the gap between the pole pieces and the shaft, increasing the saturated magnetism of the magnetic fluid, increasing the strength of the magnet, decreasing the cross-sectional area of the pole pieces where they contact the magnetic fluid, or any combination thereof serves to increase the sealing pressure and failure pressure of the magnetic fluid seal.

The sealing pressure and failure pressure may be optimized or tuned by adjusting each of these parameters to yield a robust seal that remains intact against the desired working pressure, but fails at the higher differential pressures achieved during sterilization, and then re-forms to normal conditions after sterilization.

The face of the pole pieces could have features incorporated that serve to hold extra magnetic fluid which could flow into the gap between the pole piece and the shaft. As a nonlimiting example, the flat surface of the pole pieces may be carved out or contoured to provide a void that acts as an overflow region. Since fluid may be washed out during operation or displaced during sterilization, it may be desirable to have such features holding extra magnetic fluid (e.g. FIGS. 1C & 1D). The reservoir features could hold magnetic fluid that is displaced from the fluid region under high differential pressure or hold surplus magnetic fluid to replenish the magnetic fluid in the fluid region. MF reservoir region features may be shaped to connect with the MF region and to use, without limitation, physical effects like inertia, magnetic fields, or surface tension to enhance the capture of displaced magnetic fluid or the distribution of surplus magnetic fluid. Reservoir features may be present on either face of the pole piece. In some embodiments, pole pieces may be shaped to create an internal MF fluid reservoir (e.g. FIGS. 1H and 1I). In some embodiments, pole pieces with reservoirs may be designed so surface tension or magnetic forces hold the magnetic fluid in the MF reservoir region that allows sterilization and the action of spinning the motor distributes the magnetic fluid to the intended MF region required for sealing the motor. In other embodiments, the pole pieces may use a material that expands on contact with liquid (e.g. a hydrogel) to push the magnetic fluid from the MF reservoir region to the MF region once the motor is immersed.

In a nonlimiting example, tested pole pieces were machined from 420F stainless steel. In some embodiments, pole piece shapes may be incorporated into magnets so that no separate pole pieces are required (e.g. FIG. 1G).

In some embodiments, it may be desirable to coat the pole pieces with a hard material to minimize wear if the system is subjected to shocks, which may result in intermittent contact between the shaft and the pole pieces.

Gas Paths

In some embodiments, small channels may be present to connect all internal regions of the pump or device that would otherwise be isolated from each other by the MF seals. In some embodiments, these channels may pass through each pole piece, such through a thickness of the pole pieces. In other embodiments, they may pass through the housing. Other embodiments are possible.

Shield

In some embodiments, the MF seal design may comprise one or more shields that reduce the dynamic flux in the interface between the magnetic fluid and the liquid the pump or device is immersed in. Such shields may comprise components that are fixed in relation to the shaft or the housing (e.g. FIG. 1E). In some embodiments, the shield may comprise additional reservoir features. In some embodiments, the shield feature may be incorporated into the pole piece design (e.g. FIG. 1G). In general, more than one shield may be present and multiple shields may be located apart from one another. For example, in a multi-stage MF seal, one or more shields may be associated with each MF seal stage.

Temporary Components

In some embodiments, the motor may be assembled with a temporary component that confines the magnetic fluid to an initial location to allow sterilization, such as the MF reservoir or the like. Following sterilization, the temporary component may be removed to allow the magnetic fluid to move to the desired fluid region for effective sealing, such as the MF region or an area near the MF region that allows the magnetic fluid to move into the MF region when the device is in operation. Such temporary components may be simple sleeves (as shown in FIG. 1J and 1K) or magnets located externally to the motor housing.

Sterilization Optimization

In some embodiments, the sterilization process may be performed by placing the pump or the like into a sterilization chamber. Referring to FIG. 3, the sterilization chamber may be filled with a sterilization gas and may adjust pressure in the chamber to allow the gas pathway show by arrows to form. The pump or the like may provide any of the various MF seal embodiments discussed previously. When the sterilization chamber is activated, it causes a change in pressure that ruptures the MF seal. The rupture of the MF seal allows ingress or egress a sterilization gas through the MF seal. Once sterilization is complete, the gas injection or evacuation device may be deactivated to allow the MF seal to re-form.

An advantage of the existing design is that it allows for sterilization by conventional methods (e.g. steam, gamma, or EtO gas). Device designs that allow the seal to be interrupted during sterilization, but reformed after sterilization or initially formed after sterilization are valuable because they allow the interior (region sealed off by the magnetic seal) of the motor to be easily sterilized. This ensures the pump cavity is sterile, thus yielding a safer design if the seal were to fail during implantation or while implanted. Note this requires that the seal can be formed or reformed after sterilization without compromising the sterilized state of the external surfaces of the device.

As a nonlimiting example, during high pressure gas injection (e.g. EtO) or low pressure (vacuum) evacuation, the seal can "rupture" and allow the ingress and egress of the EtO gas for sterilization. After returning to atmospheric pressure, the seal can re-form, even if some or all of the magnetic fluid has been displaced from the sealed region by the sterilization cycle. Certain embodiments could incorporate reservoirs and possibly other features to retain the magnetic fluid so that once the system returns to normal pressure, the seal will re-form (FIGS. 1C-1D).

In one embodiment, the pole piece furthest away from the impeller can be the only element hermetically sealed to the pump, which can create alternative gas paths for gas-based sterilization both for evacuation and gas injection that do not require the magnetic seals to fail to sterilize the area between them. Referring to FIG. 3 as a nonlimiting example, the arrows illustrate gas paths that allow the sterilization of region B even if the magnetic seals do not fail. In other embodiments, the silicone adhesive may or may not be applied so as to leave gas paths that also allow the sterilization of air space C. In some embodiments, the gas paths may be small enough to quickly foul when immersed in blood during operation or to exclude certain blood components (e.g. platelets) or liquid entirely.

In certain embodiments, a temporary magnetic trap could be incorporated that is applied during gas sterilization to pull the magnetic fluid away from the pole pieces and allow an open gas path in and out of the pump. This trap could then be removed prior to operation of the pump, thereby allowing the MF seal to form or reform prior to implantation. Certain embodiments of such temporary magnetic traps could use permanent magnets or electromagnets.

In certain embodiments, the seal could be constructed with a housing that is permeable to gases, but not liquids (e.g. materials commonly used in sterilization pouches), so that the inner cavity of the pump can be sterilized without compromising the seal integrity.

The seal could also be constructed with a housing that is gas permeable and initially liquid permeable, but quickly fouls to become impermeable to gas, liquid, or both when exposed to biologic fluids (e.g. blood/serum). This allows gas-based sterilization prior to exposure to biological fluids. As one nonlimiting example, holes through the housing to the otherwise sealed portion of the motor would allow gas ingress and egress during sterilization, but would quickly be sealed with clotted blood once the device is implanted due to a small size of the holes.

Multistage Seal

The magnetic fluid seal could be constructed of multiple magnetic fluid stages in series to increase the sealing pressure obtained. This could be achieved by using multiple sets of seal cartridges (which comprise the magnet and pole pieces arrangement discussed previously above), all coaxial with the shaft and longitudinally arrayed on the shaft.

Hybrid Seal

The magnetic fluid seal could be combined with other sealing elements such as, but not limited to, face seals, lip seals, and labyrinth seals either upstream or downstream of the magnetic fluid seal (or both).

In one embodiment, a magnetic fluid seal could serve to capture any wear particles generated by a traditional mechanical seal. When the magnetic fluid seal is located close to the impeller, any wear particles that are produced from the mechanical seal could be retained by the magnetic fluid seal. Such an arrangement could also capture particles generated by bearings or other mechanical contact points.

In another embodiment, a magnetic fluid seal may be utilized in combination with any seal suitable for preventing fluid intrusion during operation (e.g. labyrinth seal). The magnetic fluid seal could serve to prevent fluid intrusion to the pump while the shaft is not-rotating, and the other seal (e.g. labyrinth seal) would prevent fluid intrusion (on its own or in combination with the magnetic fluid seal) during pump operation.

As a nonlimiting example, the miniature magnetic fluid (MF) seal is composed of a magnet. For example, without limitation, a rare earth magnet like NdFeB, but other types of magnets of suitable strength may be used in other embodiments. In some embodiments, the magnet may have a Br (Residual Magnetic Flux Density) 500 mT or higher. In some embodiments, the magnet may have a Hc (Coercive Force) −350 kA/m or lower. As a nonlimiting example, the strong magnetic may be a 4×2×1 mm magnet, but other sizes may be used in other embodiments. The strong magnet may be sandwiched between two ferromagnetic pole pieces. As a nonlimiting example, the pole pieces may be 4×1.1×0.5 mm, but other sizes may be used in other embodiments. In some embodiments, a shield, which may be nonmagnetic, is placed on the pole piece facing the liquid to prevent MF from leaking from the seal area. As a nonlimiting example, the shield may be a 4×1.2×1.5 shield, but other sizes may be used in other embodiments. The seal is installed on a small ferromagnetic shaft. As a nonlimiting example the shaft may be 1 mm in diameter, but other sizes may be used in other embodiments. The MF seal is formed by injecting MF into the gap between the pole pieces and the shaft. The MF used in one nonlimiting example was Exp. 15067 (Ms: 47.8 kA/m and η: 0.5 Pa·sec), but other MFs with suitable properties may be used. In one nonlimiting example, total volume of the MF seal is 44 μL, but other embodiments will have different total volumes.

From the discussion above, it shall be apparent to one of ordinary skill in the art that a variety of device arrangements and methods of operation are possible. As discussed further herein nearly any combination of the various features discussed above may be implemented.

In one embodiment, the Magnetic Seal is positioned between the housing and the shaft of a motor and may include a combination of one or more of the features discussed further below:

At least one magnet positioned inside the housing and around the shaft

At least one pole piece formed from or in contact with the at least one magnet and shaped to form an annular gap with the shaft A magnetic fluid that fills the one or more annular gaps between the one or more pole pieces and the shaft Wherein components of the magnetic seal respond to a change in pressure exceeding a predetermined amount by opening one or more pathways that allow gas access to access regions (e.g. MF region, protected device region, MF reservoir region, or combinations thereof) inaccessible at pressures under the predetermined amount. In some embodiments, such pathways are small enough to quickly clot when exposed to blood.

A magnetic fluid reservoir to capture magnetic fluid from the annular gap or replenish magnetic fluid to the annular gap In some embodiments, the arrangements discussed above and herein may be modified to provide a gap between the housing and the magnets and/or pole pieces A magnetic fluid that remains outside the annular MF region, such as in the MF reservoir, while the motor is not spinning, but moves into the MF region when the motor spins A magnetic fluid that remains outside the annular MF region while the motor is dry, but moves into the MF region when the motor is immersed in liquid Description of Preliminary Experiments and Results A miniature MF seal was assembled in a motor casing. This assembly was loaded into a test fixture to monitor the external air pressure that the seal could withstand. Initially, the seal was tested with a static (non-rotating shaft), and external air pressure was increased gradually and monitored with a digital sensor. Subsequent to this experiment, sealing pressure was measured with a rotating shaft at speeds up to 40,000 rpm. Sealing pressure was measured as before. A sealing pressure of above 370 mmHg was obtained at all motor speeds of 0 to 40,000 rpm.

Feasibility of the seal for a fluid-immersed operating condition was assessed by submerging the seal in saline at a mean pressure of 81 mmHg. The pump was operated at a speed of 25,000 rpm, which resulted in a flow rate of 1.5 L/min. The seal remained intact with no leaks observed for 10 days of pump operation.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. A magnetic fluid seal system, the system comprising:
   a rotating shaft of an implantable device;
   a housing of the implantable device, wherein the shaft is positioned within the housing; and
   a magnetic fluid (MF) seal positioned on the shaft within the housing, wherein the MF seal isolates a first end from fluids at a second end, and the MF seal comprises
      a magnet positioned about the shaft, wherein the magnet is cylindrically shaped,
      at least one pole piece positioned about the shaft, wherein the magnet is in contact with the at least one pole piece,
      a magnetic fluid present in at least a portion of an annular gap between the shaft and the at least one pole piece and/or the magnet, wherein the magnetic fluid prevents other fluids from passing through the annular gap, and
      a shield that is nonmagnetic and positioned about the shaft adjacent to the at least one pole piece to isolate the first end from the fluids at a second end, wherein the shield and the at least one pole piece define a reservoir space for excess magnetic fluid.

2. The system of claim 1, wherein the shield is shaped to provide the reservoir space for the magnetic fluid.

3. The system of claim 1, wherein the at least one pole piece is patterned to provide the reservoir space for the magnetic fluid.

4. The system of claim 1, wherein an internal diameter or an outer diameter of the at least one pole piece is beveled or double beveled toward outer surfaces to form a pointed tip.

5. The system of claim 1, wherein the at least one pole piece is shaped to provide a channel oriented radially to serve as an internal magnetic fluid reservoir.

6. The system of claim 5, wherein the channel is ring-shaped.

7. The system of claim 5 further comprising a hydrogel positioned in the channel, wherein the hydrogel expands on contact with a liquid and pushes the magnetic fluid into the annular gap.

8. The system of claim 1, wherein the at least one pole piece comprises three pole pieces;
   the magnet is a first magnet and the MF seal further comprises a second magnet, wherein the three poles and the first and second magnets are arranged on the shaft in an alternating manner.

9. The system of claim 1, wherein when a sealing pressure is exceeded, the magnetic fluid migrates from a magnetic fluid region to allow sterilization.

10. The system of claim 1, wherein the MF seal provides gas paths.

11. A method for sterilizing an implantable device, the method comprising:
    placing the implantable device in a sterilization chamber, wherein the implantable device comprises
       a rotating shaft for the implantable device,
       a housing of the implantable device, wherein the shaft is positioned within the housing, and
       a magnetic fluid (MF) seal positioned about the shaft within the housing, wherein the MF seal isolates a first end from fluids at a second end, and the MF seal comprises
          at least one pole piece positioned about the shaft, wherein an internal diameter or an outer diameter of the at least one pole piece is beveled or double beveled,
          a magnetic fluid present in at least a portion of an annular gap between the beveled or the double beveled internal diameter of the at least one pole piece and the shaft, wherein the magnetic fluid prevents other fluids from passing through the annular gap, and
          a shield that is nonmagnetic and positioned about the shaft adjacent to the at least one pole piece to isolate the first end from the fluids at a second end, wherein the shield and the at least one pole piece define a reservoir space for excess magnetic fluid;
    activating the sterilization chamber to cause a rupture of the MF seal, wherein the rupture allows ingress or egress a sterilization gas through the MF seal; and
    deactivating the gas injection or evacuation device to allow the MF seal to re-form.

12. The method of claim 11, wherein the shield is shaped to provide the reservoir space for the magnetic fluid.

13. The method of claim 11, wherein the at least one pole piece is patterned to provide the reservoir space for the magnetic fluid.

14. The method of claim 11, wherein an internal diameter or an outer diameter of the at least one pole piece is beveled or double beveled toward outer surfaces to form a pointed tip.

15. The method of claim 11, wherein the at least one pole piece is shaped to provide a channel oriented radially to serve as an internal magnetic fluid reservoir.

16. The method of claim 15, wherein the channel is ring-shaped.

17. The method of claim 15 further comprising a hydrogel positioned in the channel, wherein the hydrogel expands on contact with a liquid and pushes the magnetic fluid into the annular gap.

18. The method of claim 11, wherein the at least one pole piece comprises three pole pieces;
    the magnet is a first magnet and the MF seal further comprises a second magnet, wherein the three poles and the first and second magnets are arranged on the shaft in an alternating manner, and an opposing pole of each of the first and second magnets face each other.

19. The method of claim 11, wherein the MF seal provides gas paths to allow the sterilization.

20. The method of claim 11, further comprising a temporary shaft sleeve to confine the magnetic fluid from a magnetic fluid region and to allow a gas path for sterilization.

* * * * *